(12) United States Patent
Bencomo et al.

(10) Patent No.: US 6,765,091 B1
(45) Date of Patent: Jul. 20, 2004

(54) OLIGOSACCHARIDES DERIVED FROM RIBOSE-RIBITOL-PHOSPHATE, AND VACCINES CONTAINING THEM

(75) Inventors: Vicente Guillermo Vérez Bencomo, Ciudad Habana (CU); Rene Roy, Gatineau (CA)

(73) Assignees: Universidad de la Habana, Habana (CU); University of Ottawa, Ottawa (CA)

( * ) Notice: Subject to any disclaimer, the term of this patent is extended or adjusted under 35 U.S.C. 154(b) by 0 days.

(21) Appl. No.: 10/070,101
(22) PCT Filed: Aug. 15, 2000
(86) PCT No.: PCT/CU00/00003
§ 371 (c)(1), (2), (4) Date: Jul. 16, 2002
(87) PCT Pub. No.: WO01/16146
PCT Pub. Date: Mar. 8, 2001

(30) Foreign Application Priority Data
Aug. 30, 1999 (CU) ................................. 121/99

(51) Int. Cl.$^7$ ........................... C07H 3/06; C07H 11/04
(52) U.S. Cl. ................... 536/124; 536/1.11; 536/55.1; 536/123.1
(58) Field of Search ................ 536/1.11, 55.1, 536/123.1, 124

(56) References Cited

FOREIGN PATENT DOCUMENTS

| EP | 0320942 | * | 6/1989 | ........... C07H/15/04 |
|----|---------|---|--------|----------------------|
| WO | WO 94/00149 | * | 1/1994 | ........... A61K/39/00 |

\* cited by examiner

Primary Examiner—Samuel Barts
Assistant Examiner—Ganapathy Krishnan
(74) Attorney, Agent, or Firm—Lackenbach Siegel, LLP

(57) ABSTRACT

The present invention relates to the field of the Medicine, in particular with the chemical synthesis of oligosaccharide mixtures derived of ribose-ribitol-phosphate, which are used as active principle in vaccines for the prevention of infections caused by *Haemophilus influenzae* type b (Hib), as well as with the vaccines containing said oligosaccharide mixtures.

The oligasaccharide mixtures obtained by chemical synthesis of the present invention, comprise repeating units of formulae (phosphate-ribosa-ribitol)n or (ribose-ribitol-phosphate)n of at least 5 compounds of structure A or B, which represent the repeating unit of the capsular polysaccharide of *Haemophilus influenzae* type b and differ only by n, being n a value contained between 4 and 25 (n≧4 y≦25), and wherein $R_1$ or $R_2$ is a spacer for conjugation to a carrier, with the condition of $R_1$=spacer if $R_2$=H, or $R_2$=spacer if $R_1$=H.

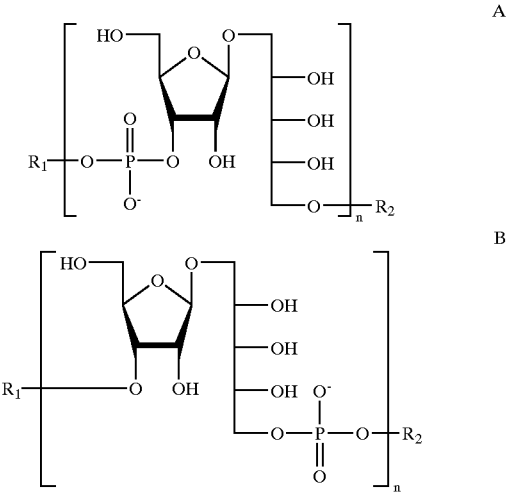

The invention also is related with the immunogens containing such oligosaccharide mixtures, with the vaccines containing said immunogens and with the methods to prepare these oligosaccharides as mixtures. Furthermore, the invention includes the use of the vaccines, alone or combined with other vaccines, for the prevention of the infections caused by *Haemophilus influenzae* type b.

7 Claims, 6 Drawing Sheets

OLIGOSACCHARIDES DERIVED FROM RIBOSE-RIBITOL-PHOSPHATE, AND VACCINES CONTAINING THEM

TECHNICAL SECTOR

The present invention relates to the field of the Medicine, in particular with the chemical synthesis of oligosaccharide mixtures derived of ribose-ribitol-phosphate, which are used as active principle in vaccines for the prevention of infections caused by *Haemophilus influenzae* type b (Hib), as well as with the vaccines containing said oligosaccharide mixtures.

PRIOR ART

*Haemophilus influenzae* type b is a serious human health problem worldwide. The bacterium causes, mainly in children under the age of 5, meningitis, pneumonia, epiglotitis, and other diseases of the respiratory tract. The sequels observed, ranged from auditive problems until sever is mental retardation, attain in many countries more than 30% of the survivors from the disease. Recent estimates of World Health Organization indicated that more than 550 000 children dies annually from the diseases caused by *Haemophilus influenzae* type b in the world.

Purified capsular polysaccharide of *Haemophilus influenzae* is able to induced protective immunity in adults, however the immune response in children is very poor and practically absent in infants under 2 years old.

The capsular polysaccharide has the following structure:

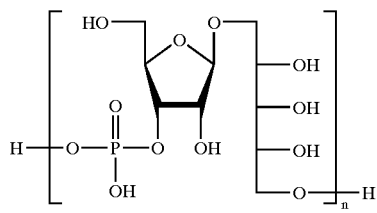

It has been demonstrated that the main problem is the antigen's nature itself, due to being a polysaccharide, it is a T-independent antigen unable to stimulate infant immune system, still immature. There was demonstrated that the solution to this problem can be achieve by linking covalently (conjugating) the polysaccharide to a protein known as carrier. The product thus obtained, known as conjugated vaccine, induces antibody protecting level from two months of age.

Chu et al., (Infection immunity 1983, 40, 245–256) obtained the conjugate from the native capsular polysaccharide and tetanus toxoid after activation with cyanogen bromide.

Gordon (U.S. Pat. No. 4,496,538) activated the natural polysaccharide with cyanogen bromide and then conjugated it to difteria toxoid through the adippic acid dihidrazide.

Hilman et al. (U.S. Pat. No. 4,459,286) conjugated the natural polysaccharide through 6-aminocaproic acid to menongococcal outer membrane protein after their initial activation.

In all the previous conjugation processes, the covalent linkage takes place between several groups of the capsular polysaccharide and the carrier protein.

The ability to induce a protecting immunity in infants depends on the structure of the conjugate. When the conjugation is performed on the native polysaccharide, the groups participating in the linkage are randomly distributed alone the polysaccharide chain, making characterization of each batch very complex.

All these vaccines are very difficult to analyze by physic-chemical methods; therefore the common practice is the evaluation of each batch through studies of immunogenicity in experimental animals. However, the behavior of the conjugate is different in children than in experimental animals.

According to World Health Organization (WHO) criteria of stable quality (M. R. Holliday, C. Jones, Biologicals, 1999, 27, 51–53) the control of conjugated vaccines should be based on physic-chemical methods demonstrating similarity from one batch to another.

In order to facilitate this task, conjugated vaccines should be more and more defined at the molecular level. One alternative solution to this problem is the synthesis of capsular polysaccharide fragments. The process for the construction of the *Haemophilus influenzae* type b antigen by synthesis has two main steps, the synthesis of the disaccharide intermediate and its oligomerization. Several approaches have been developed for this synthesis.

Beuvery at al. (European patent application EPO 0276 516; U.S. Pat. No. 5,034,519; Tetrahedron Lett. 28, 1553, 1987) and Hoogerhout et al. (J. Carbohydr. Chem, 7, 1988, 399–416) obtained by synthesis a fragment of the capsular polysaccharide that was claimed as containing between 3 to 20 repetitive units. To achieve this goal the disaccharide intermediate 2 was first prepared and then through solid-phase chemistry or solution synthesis, an oligomer containing 6 repeating units was prepared (Elie et al., Rec. Trav. Chim. Pays-Bas 108, 1989, 219). The oligomers were conjugate to proteins or peptides through a spacer. The conjugate trimer was as immunogenic in mice than commercially available vaccine prepared from the capsular polysaccharide.

In a preferred embodiment illustrating synthetic pathway followed, the subsequent strategy was used: 1-synthesis of the ribitol, 2-coupling to ribose, 3-selective introduction of substituents in the ribose unit and 4-introduction of the phosphor-activating group. Using this pathway the key disaccharide derivative 2 was obtained in only 15 reaction steps.

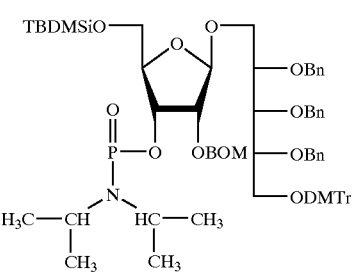

The overall yield is 7% (Hermans et al., Recl. Trav. Chim. Pays-Bas 1987, 106, 498–504). Furthermore, this process has two major drawbacks: the process includes 11 chromatographic steps and the protecting groups of the key intermediary are not ideal for the oligomerization process.

In the oligomerization, or second step of the synthesis, the method used is solution synthesis through activation by phosphotriester, allowing yields between 70–90% per cycle, based on the disaccharide. The main drawback of such procedure is the impossibility of preparing fragments containing more than 4 repeating units, because the yields decrease dramatically. The disaccharide intermediate 2 has three different protective groups, making very difficult the deprotection of the final product. Therefore this disaccharide isn't the more convenient for oligomerization through solid-phase chemistry. Inasmuch the synthesis of an hexamer was reported.

In immunological assays (Peters CCAM, et al, Infect. Immunity 1991, 59, 3504–10) only it is reported the conjugation of a trimer to tetanus-toxoid and its immunogenicity in mice and monkeys.

G. Just, J. Upeslacis (European patent application EP 0 320 942, L. Chan; G. Just, Tetrahedron, 46, 1990, 151–162) synthesized also a fragment of the capsular polysaccharide through a disaccharide intermediate and synthesis in solution chemistry. With the aim of preparing the optimal intermediate for the synthesis of the antigen, a different pathway was selected: 1-synthesis of ribitol, 2-synthesis of the ribose unit with adequate protecting groups, 3-coupling of ribose and ribitol and 4-introduction of the phosphor active functionality.

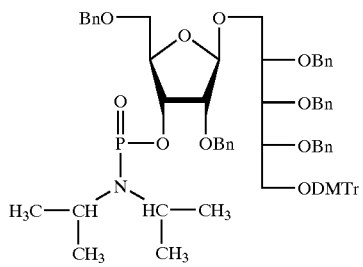

3

Using this methodology a procedure for the intermediate 3 as phosphoramidite displaying a better selection of protecting groups for the oligomerization procedure. In order to attain this objective, a bigger number of steps were necessary. The key derivative was attained in 19 steps and with the use of 8 chromatography processes of purification.

The disaccharide 3 was oligomerized in solution giving fragments of the capsular polysaccharide containing 3 repeating units with yields based on disaccharide between 70–90% per cycle.

Kandil et al. (Syn. Lett., 1992, 555–7), Chon et al. (PCT patent application WO93/15205 y U.S. Pat. No. 5,679,352), synthesized a fragment of the capsular polysaccharide using the same disaccharide intermediate 3 and through solid-phase chemistry, using as support monomethoxypolyethylenglycol obtained fragments containing up to 6 repeating units, the yield per cycle was 95%.

Krivan, et al.. (PCT patent application WO94/00149) and Nilsson, et al. (J. Carbohydr. Chem. 10, 1991, 1–22) obtained a fragment of 10 repeating units with a similar disaccharide intermediate and solid-phase chemistry. This fragment was conjugated through a spacer to Hib adhesin. The phosphonate intermediate was obtained in 21 steps with an overall yield of 5%. At least 7 chromatographic steps were also needed. The oligomerization process was performed using H-phosphonates and solid-phase chemistry using Merrifield aminated resin. The antigen was obtained with incorporation of 97–99% per cycle.

Chiu Machado et al. (J. Carbohydr. Chem., 13 1994, 465–474) and Cuban patent 22424 reported an efficient procedure for the synthesis of a suitable protected ribose derivative from glucose. Using this derivative they prepared the key disaccharide in 20 reaction steps.

One of the aspects that make difficult the application of the synthesis to the preparation of the Hib fragments and their use in vaccines is the synthesis of the disaccharide intermediate.

All the methods listed above reflex the state of the art of modern carbohydrate chemistry, however they have two major serious technical drawbacks. The use of several chromatographic steps through the synthesis that make unpractical the synthesis at industrial scale, and the number of synthetic steps that is usually very high. The main problem for the synthesis of the disaccharide in fewer reaction steps is the introduction of benzyl groups in the ribose unit.

The oligomerization process of the disaccharide intermediate could be performed either in solution, with the serious inconvenient that the maximal size that could be attained is limited to 3–4 repeating units. It could be performed also by solid-phase chemistry. Solid-phase chemistry allows the preparation of oligosaccharides ranging from 6 to 10 repeating units with high yeilds per cycle. However the two serious problem usually present are that the real yield is only 10–15%, because for attaining high incorporation of a disaccharide intermediate per cycle, a high excess of disaccharide, between 3 to 10 mol-equivalent is usually required. The excess of disaccharide is loose during the process. Another problem is that two different derivative are usually required, one for coupling to the solid support and the second for the elongation of the chain.

The synthesis of a single pure oligosaccharide fragment devoid of any difference not only in its structure but also in the chain length is a common aspect to all the precedent reports on the synthesis of Hib antigens, and at the same time, was one of their principal objectives. All this was based on the assumption that the antigen composed by a single molecule is necessary to attain anti-Hib conjugate vaccines with more stable quality, due to an easier control.

New methods were developed for the preparation of oligosaccharide fragments by the fragmentation of natural polysaccharides and also for the activation of the oligosaccharide mixture by one of their terminal position.

In U.S. Pat. Nos. 4,808,700; 4,761,283, as well as in Glycoconjugate J., 1989, 6, 489–498 (R. C. Seid, et al.) the natural polysaccharide is oxidised with peryodate and purified the fragments obtained. The mixture of oligosaccharide fragments become activated by the two terminal positions as shown in the following scheme. These oligosaccharides were conjugated through a reductive-amination reaction to CRM 197. As it can be seen from the scheme, both conjugation sites are different. Once the conjugation was performed at least two families of conjugated oligosaccharides with different structures will exist. On the other hands a percent of the oligosaccharide non very well determine results from the linkage of the same oligosaccharide to two different sites of the same protein or to two different molecules of protein. All these phenomena generate heterogeneity and make difficult the control.

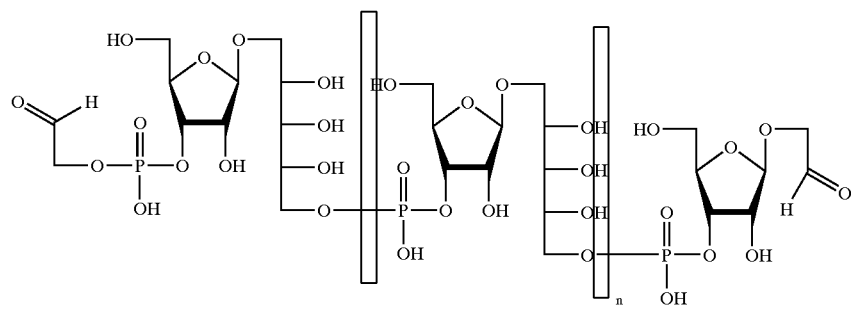

On the other hand, in U.S. Pat. No. 5,153,312, as well as Vaccine 1999, 17, 1251–63 (P. Constantino et al.) it is reported the hydrolysis of the natural polysaccharide with acetic acid and purification of the resulting mixture of oligosaccharide fragments. The product is activated through a sequence of reactions where the spacer is introduced through a reductive amination with ethylendiamine at high pH and temperature that can affect the integrity of the oligosaccharide mixture. On the other hand, a proportion of the antigen is probably inactivated after its reduction of their carbonyl hemiacetal as shown in the following scheme. Further, the oligosaccharide amine derivative was selectively substituted with the active ester of adipic acid by one of their terminal ester function. The other ester function remains active for the coupling to a protein.

perform fragmentation of the natural polysaccharide followed by the introduction of a functional active group and attain the same level of molecular definition and purity in the antigen that it can be get by chemical synthesis There are not apparent advantages in the control of conjugate vaccines with the use either of a oligosaccharide with a define size or a mixture of oligosaccharides by size but homogeneous by the rest of their structure. This had been demonstrated with the advance experimented by analytical methods of the state of the art which makes very easy to determine the composition of Hib oligosaccharide mixture (P. Constantino, et al., Vaccine 1999, 17, 1251–1263 and D. Prioeti, et al., European Carbohydrate Symposium, Galway, July 1999, PB014).

On the other hand, there are not differences in the immunological behavior between a vaccine composed by a mix-

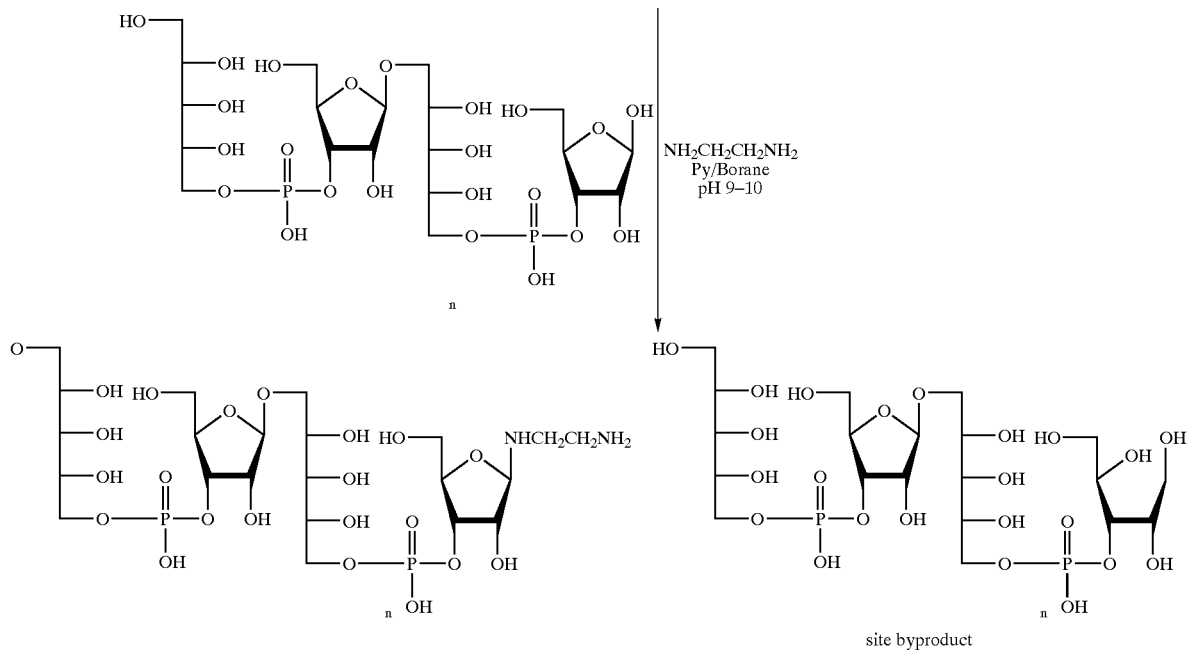

site byproduct

The two vaccines prepared from products of fragmentation of the natural polysaccharide have been used in the practice of immunization of large mass of children. This have demonstrated that it is possible to use oligosaccharide, without a single size, but rather in the range of size, in the manufactured of conjugate vaccine against Hib and, at the same time, to control adequately the reproducibility and the quality of the product. Even if the conjugate obtained by this way are more defined than those obtained by direct activation of the polysaccharide, it is practically impossible to ture by size of Hib oligosaccharides or by a single size oligosaccharide when the fragment are bigger than 3 repeating units (S. Pillai, et al., Infection and Immunity, 1991, 59, 4371–6; A. A Kandil, et al., Glycoconjugate J., 1997, 14, 13–7 and Peters CCAM, et al., Infect. Immunity 1991, 59, 3504–10).

Additional circumstances difficult the selection of an optimal single size from all the points of view. The oligosaccharides from 4–6 repeating units are synthesized more easily and their size is usually enough to induce an adequate immune response. However, the quantity of carrier protein necessary for this vaccine is very high and the stability of the oligosaccharide in the vaccine is poorer, due to the degradation process through the hydrolysis of the phosphodiester provokes very rapidly a very short fragment coupled to a protein with less than 4 repeating units, and therefore inactive. The fragments with a size between 8–20 repeating units are in principle more stable because after degradation to half of their size, the remaining fragment coupled to the carrier protein will be bigger than 4 repeating units. The quantity of carrier protein necessary for a vaccine doses is also smaller.

However, according to the state of the art for the oligosaccharides of Hib, the synthesis of fragments of size ranged between 10–20 is impossible by solution methods, and is still a challenge by solid phase methods. In fact, in previous reported examples, the oligosaccharides of this size are completely absent. Another disadvantage is the T-dependency of the immune response, a very important aspect for attaining a good immune response in children. The T-dependence of a polysaccharide decrease with the increase in the size (C. Fernández, E. Sverremark, *Cell Immunol* 1994, 153, 67–78).

Concluding, any way of synthesis of Hib antigens to be competitive, must reduce the number of steps to the key disaccharide, to reduce the number of chromatography steps and specially to increase significantly the yields in the oligomerization process.

The mixtures of oligosaccharides obtained by hydrolysis of the natural polysaccharides, contain fractions of both size intervals, taking the advantage of each and reducing their disadvantages. If similar mixtures could be obtained by synthesis, it will take the advantage of containing both size intervals. Been designed by synthesis, this mixture will be more define and pure and will contain the spacer in a precise proportion and position.

DISCLOSURE OF THE INVENTION

The present invention is particularly related with the chemical synthesis of oligosaccharide mixtures derived from ribose-ribitol-phosphate, which are used as active principle in vaccines for the prevention of infections caused by *Haemophilus influenzae* type b (Hib), as well as with the vaccines containing said oligosaccharide mixtures.

The oligasaccharide mixtures obtained by chemical synthesis of the present invention, comprise repeating units of formulae (phosphate-ribosa-ribitol)n or (ribose-ribitol-phosphate)n of at least 5 compounds of structure A or B, which represent the repeating unit of the capsular polysaccharide of *Haemophilus influenzae* type b and differ only by n, being n a value contained between 4 and 25 ($n \geq 4$ $y \leq 25$), and wherein $R_1$ or $R_2$ is a spacer for conjugation to a carrier, with the condition of $R_1$=spacer if $R_2$=H, or $R_2$=spacer if $R_1$=H.

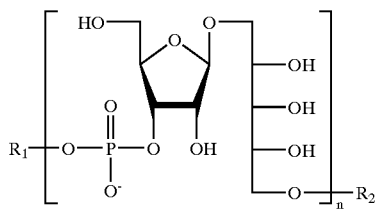

A

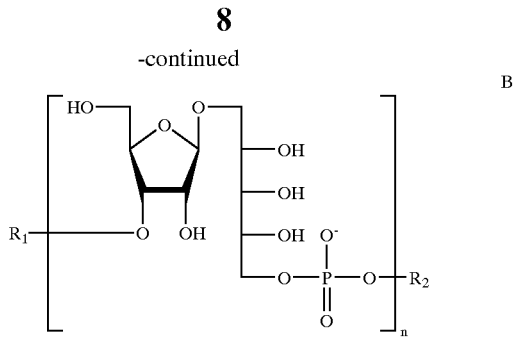

B

The invention also is related with the immunogens containing such oligosaccharide mixtures, with the vaccines containing said immunogens and with the methods to prepare these oligosaccharides as mixtures. Furthermore, the invention includes the use of the vaccines, alone or combined with other vaccines, for the prevention of the infections caused by *Haemophilus influenzae* type b.

By means of the present invention it is possible to obtain, by chemical synthesis, a regular mixture of oligosaccharides of a well defined size and in a more efficient way. This mixture has a higher purity and it is obtained using a simpler technical process. Also it has been found that the conjugated vaccines prepared from the mixture of the invention are superior due to their manufacturing and simpler in their control.

Another object of the present invention is the synthetic method to obtain the oligosaccharide mixture above mentioned, which is characterized by being a one step process consisting in a controlled polycondensation reaction between a key disaccharide intermediate, a spacer and a promoter, and characterised also by the fact that the average size of the antigen can be controlled through the proportion of each participant, their order of addition and the time of reaction.

Another object of the present invention is the use of the immunogens above mentioned in the preparation of vaccines against the diseases caused by *Haemophilus influenzae* type b, with or without the use of adjuvants and other additives.

Another of the objects of the present invention is the use of the mixtures previously described in the preparation of combined vaccines with other vaccines, conjugated or not, as for example with the vaccine against Hepatitis B, DPT, anti-meningoccocic A, B, C, anti-pneumococcic 1, 5, 6B, 6A, 14, 19F, 19A, 23F, and anti-polio.

Another object of the present invention is the optimization of the synthetic process to the key disaccharide required for the synthesis of Hib oligosaccharides. The optimization consists in the discovery of a new selective benzylation reaction that, applied to disaccharide 4, allows its transformation into disaccharide 5, with the introduction of benzyl protective groups in the ribose unit in a single step, making the whole process significantly shorter and simpler.

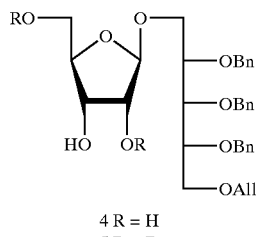

4 R = H
5 R = Bn

The object of the present invention is also the optimal procedure for the synthesis of intermediate 4 that allows its preparation with high purity in only 11 reaction steps and without the use of chromatographic processes.

Another object of the present invention is the use of the oligosaccharides previously described in the detection and quantification of antibodies anti-Hib through their conjugates with immunologically inert substances as polyacrylamide, polystyrene, latex.

The novelty of the present invention is the composition of the oligosaccharide mixture obtained, that responds to the repeating unit of the *Haemophilus influenzae* type b capsular polysaccharide with a spacer for conjugation in only one of their terminal position, in a position pre-designed in the synthesis. It responds to the same regular and homogeneous structure. The oligosaccharide mixture contains fragments from two different interval of size, mainly between 4–8 and 8–20, gaining the advantages of each interval and reducing the disadvantages that each group could have separately.

Furthermore, the novelty of the present invention is in the process itself for the preparation of such mixture through chemical synthesis, allowing the preparation of the product with high reproducibility and efficiency. In the same way, through the present invention it is demonstrated also that only one reaction lets the introduction benzyl protecting groups in the ribose unit in a single step, increasing the efficacy in the preparation of a key disaccharide derivative for the synthesis of such oligosaccharides.

The synthesis of a disaccharide intermediate begins with the preparation of a derivative 5-O-allyl-2,3,4-tri-O-benzyl-D-ribitol 14 through 9 chemical reaction represented in the following scheme. D-Ribose wax transformed in the isopropyliden derivative 6 following the procedure described previously in the art (Leonart et al., J. Het. Chem., 1966, 3, 485). The position 5 was allylated with allyl bromide under phase transfer conditions followed by hydrolysis of isopropyliden group with sulphuric acid in methanol to afford the derivative 8, that was submitted to benzylation with benzyl chloride and sodium hydride in dimethylformamide

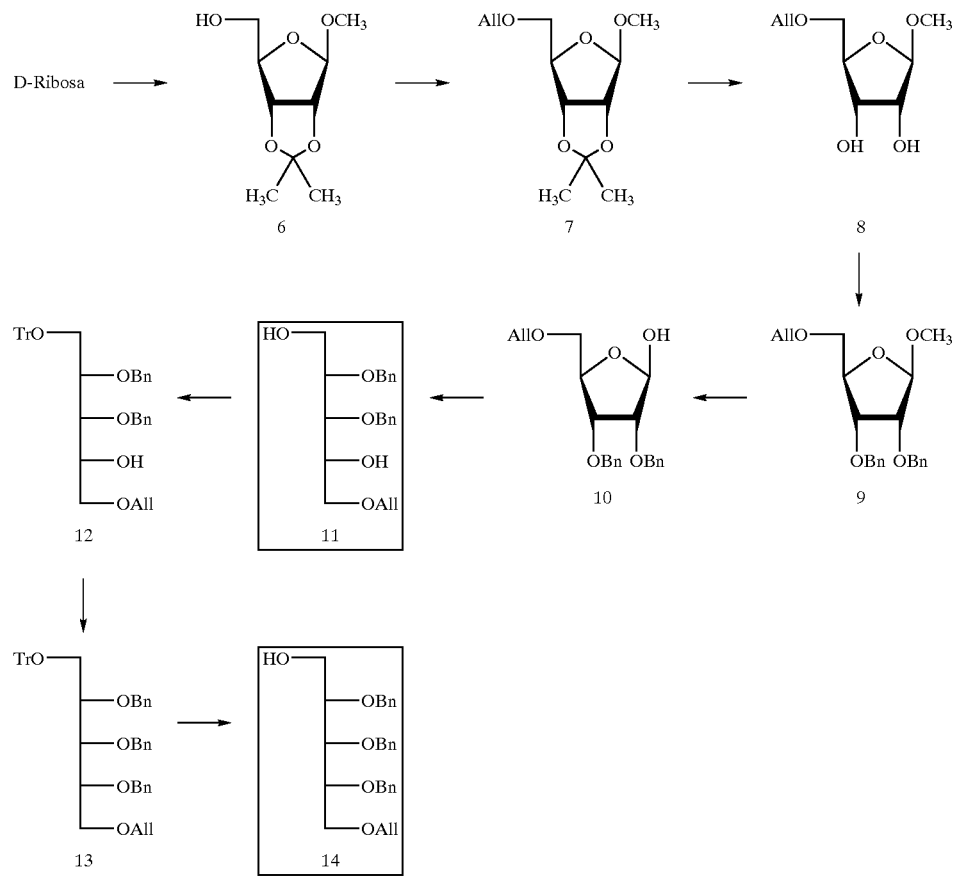

The methyl group was hydrolysed with a mixture of acetic acid and hydrochloric acid followed by reduction with sodium borhydride. The derivative 5-O-allyl-2,3-di-O-benzyl-D-Ribitol 11 was absorbed on silicagel and extracted selectively thanks to a percolation process, first with cyclohexane and then with chloroform. This procedure permits the purification in high scale, without appeal to conventional chromatographic methods.

Further, the derivative 11 was tritylated in pyridine, benzylated with benzyl chloride and sodium hydride in demethylformamide and finally hydrolysed with acetic acid to give the final ribitol derivative that was purified by distillation. The ribitol derivative 14 was ribosylated with a ribofuranose peracetate 15 as shown in the following scheme. After deacetylation followed by a new application of a absorption-desorption methods lets to reach triol 4 in high scale, without any conventional chromatographic steps.

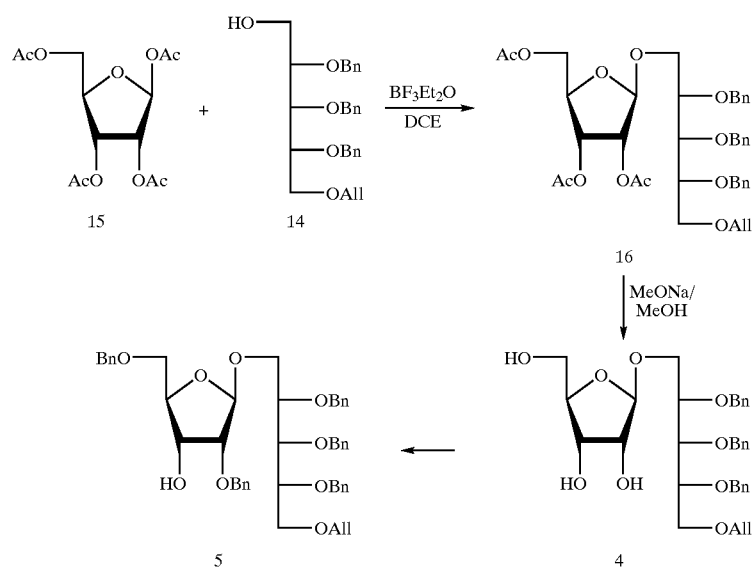

Then, it is applied the dibenzylation reaction discovery in the frame of the present invention to triol 4. This reaction lets to obtain derivative 5 after a column chromatography purification process. The allyl group of intermediate 5 was isomerised to propenyl followed by the introduction of phosphonate at the 3 free position of the ribose unit. The removal of the propenyl group gave the key intermediate derivative 19. In a similar way, the acetylation of hydroxy function at position 3 in a derivative 17, followed by hydrolysis of propenyl, introduction of the phosphonate at position 5 and deacetylation of the product, to let the key disaccharide 23 that has phosphonate at position 5 and a free hydroxy function at position 3.

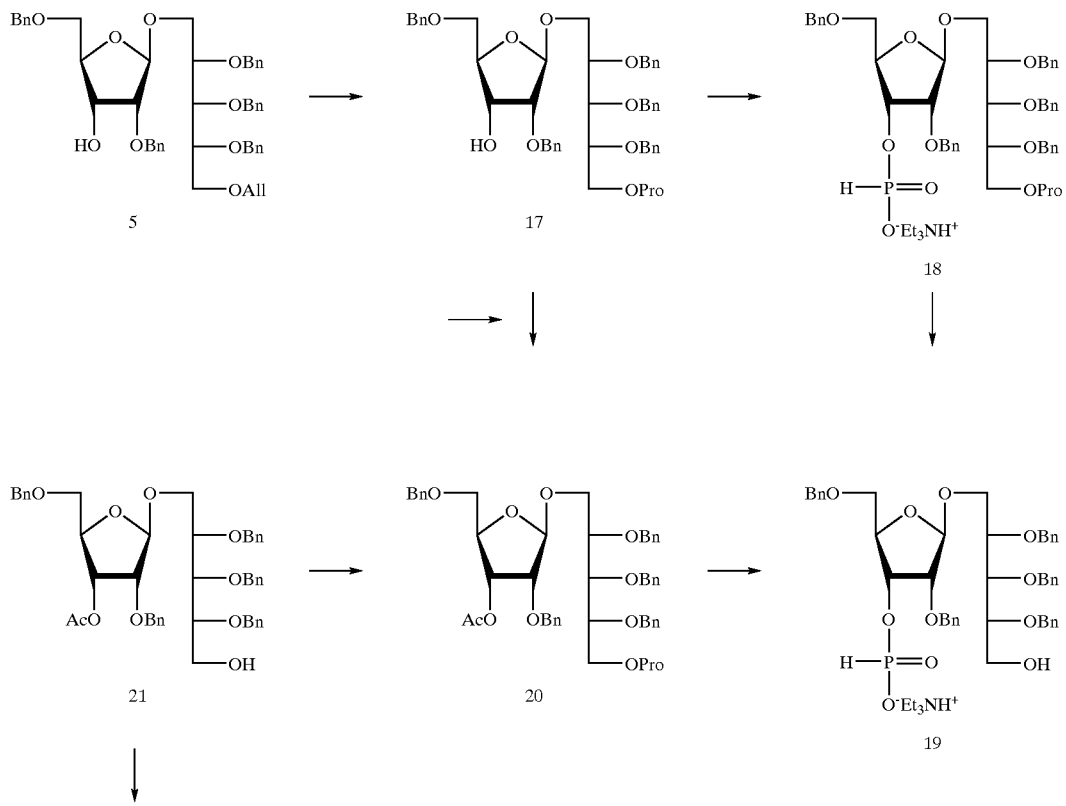

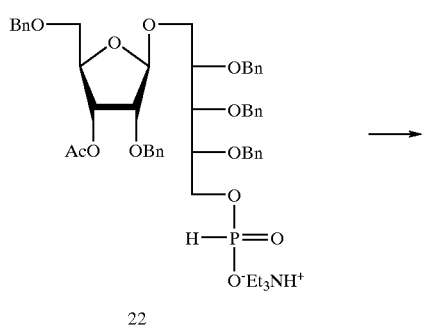
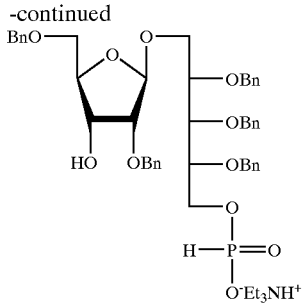

The structure of the products formed was confirmed in all cases by nuclear magnetic resonance $^1$H y $^{13}$C and by H—H y H—X correlation experiments. The purity was checked by thin layer chromatography or by HPLC.

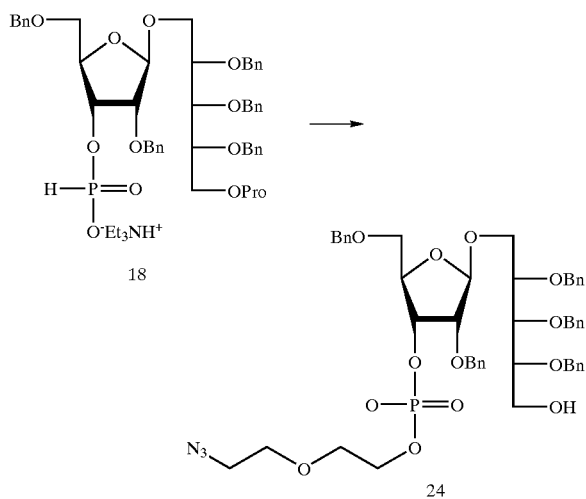

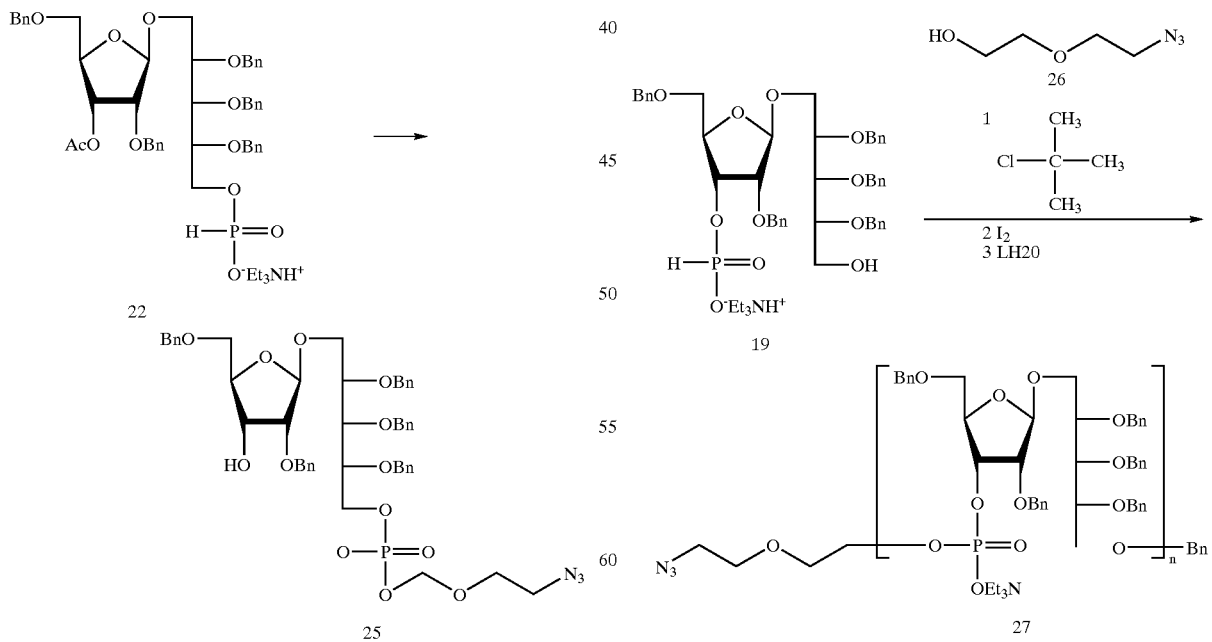

Starting from derivatives 18 or 22, they can be obtained derivatives 24 and 25 used also as acceptors in the polycondensation reaction as will be shown.

The oligomerization reaction was studied under different conditions, always on the base of only three components, a key disaccharide (19 or its analogue 23), a promoter of the reaction, that can be pivaloyl chloride, adamantane-1-carbonyl chloride or other sterically hindered acid chloride, and a third component that quench the reaction and at the same time introduce the spacer. This component contains the functional active group or its precursor in a terminal position as for example 24, 25 or 26.

As a spacer, that in the case of 24, 25 or 26 is 5-azido-3-oxapentanol, can be used any other compounds with the global formula R$_1$—Y—OH, where Y is the spacer chain that can be an aliphatic chain. The aliphatic chain can include an aromatic chain inserted in it or a number of heteroatoms oscillating between 0–5. R$_1$ is a functional group in the terminal position of the spacer and can be NH$_2$, COOR, CHO, SH or any of their precursors.

The optimal conditions for the polycondensation process were developed for several cases, for example, with the disaccharide 19, the spacer 5-azido-3-oxa-pentanol 26 and pivaloyl chloride in dichloromethane-pyridine lets to a product. A fraction contained oligomers 27 can be obtained in a yield of 70–85% base on disaccharide after oxidation, and LH-20 gel chromatography in LH-20 in methanol.

The oligosaccharide mixture 27 was hydrogenated in methanol-ethyl acetate-water-acetic acid in the presence of Palladium on carbon to give the crude oligosaccharide mixture 28. If the spacer group need to be activated, the process is better performed in the next step. For example, to the mixture of oligomers 28 was added N-hydroxysuccinimidyl ester of β-maleimidopropionic acid in dimethylformamide. After the reaction has finished, the resulting solution was diluted with distilled water, and dyafiltered under nitrogen pressure through a membrane with a 1000 cutoff. The product 30 thus obtained, is an active oligosaccharide mixture ready to be used in the conjugation process.

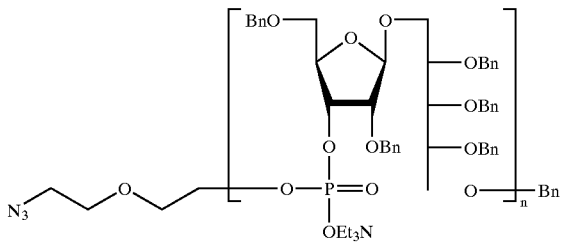
27

[H], Pd/C

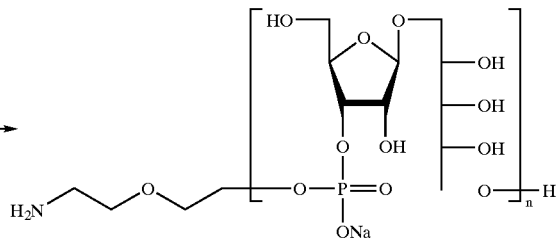
28

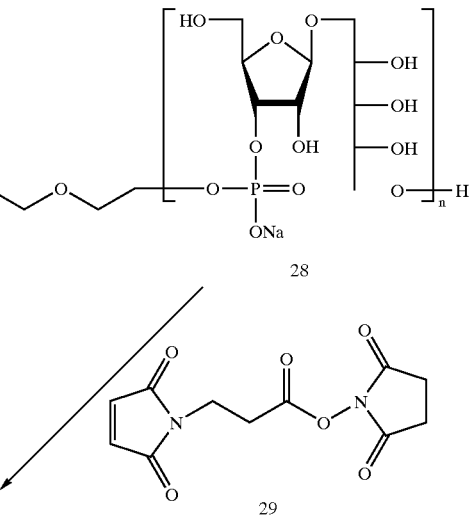
29

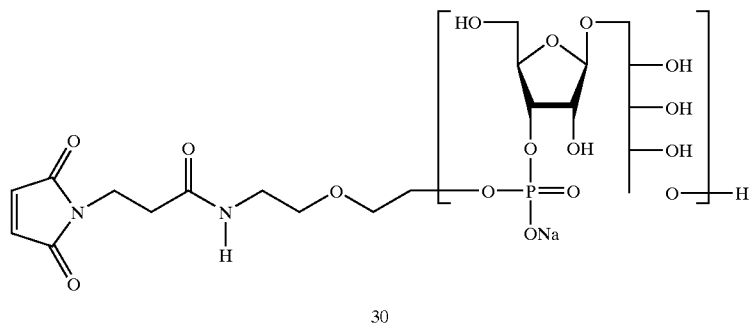
30

The structure of the products formed was confirmed in all cases by nuclear magnetic resonance $^1H$ y $^{13}C$ and by H—H y H—X correlation experiments The proteins were derivatized with thiopropionic acid, by the introduction of thiol masked as a bisulfide. For this derivatization, reagents as SPDP or DSP can be used followed by reaction with dithiotreitol in nitrogen atmosphere. The reagents excess can be eliminated for *Neisseria meningitidis* OMP or for tetanus toxoid, by precipitation with aqueous ethanol (20–95%) followed by centrifugation. For *Neisseria meningitidis* OMP the process that was carried out is illustrated in the following scheme.

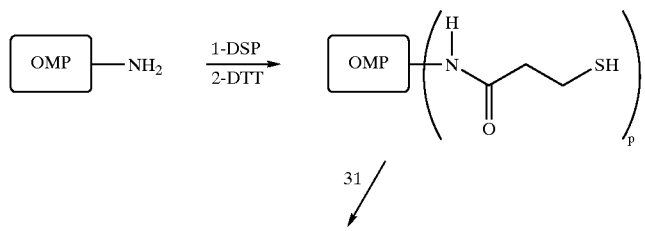
31

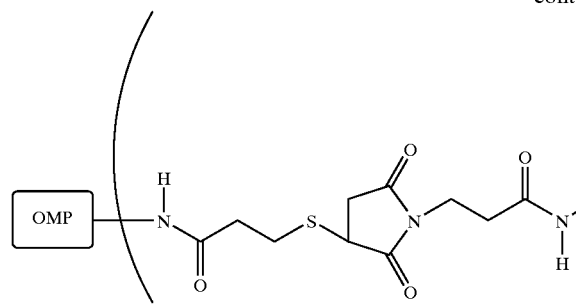 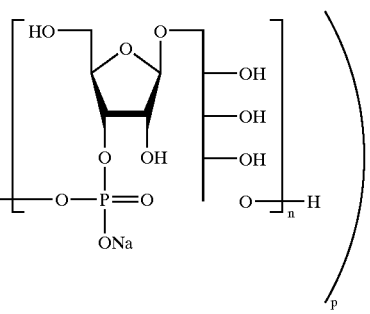

32

The thiolated protein is mixed in inert atmosphere with the active oligosaccharide, previously filtered through 0.2 microns and lyophilized. The reaction was quenched by ethanol precipitation followed by centrifugation or diafiltration Alternatively, the excess of activating reagents can be removed from the conjugate by diafiltration. Both separation processes eliminate almost all the non conjugate oligosaccharide to the protein, making the quality of the final product very stable.

The mixture of oligosaccharides 30 can be conjugate to other carrier, for example lipids. Thus, for example,k the reaction with 2,3-di-octadecyloxipropyl succinimidyl butanedioate 33 in the presence of carbodiimide lets to obtain the conjugate 34 currently used in the immunization schedule of infants under one year old. For example, mixing with the Outer Membrane Proteins from *Neisseria meningitidis* type B (OMP), a combined vaccine anti-Hib and anti-meningitis type B can be conformed. After mixing with DTP, a combined tetravalent vaccine can be obtained anti-Hib and anti-diphtheria, pertussis and tetanus.

The immunogenicity of the conjugate vaccine between oligosaccharides 30 and meningococcal outer membrane proteins was demonstrated in several animal models. The presence of antibodies against the Hib capsular polysaccharide induced by the vaccine was detected using the ELISA method (D. C. Phipps et al., J. Immunolog. Methods, 1990. 135. 121–8). The results are shown in FIGS. 2–5.

In rabbits, the vaccine formulated without alumina induces a higher response in the first doses, However both

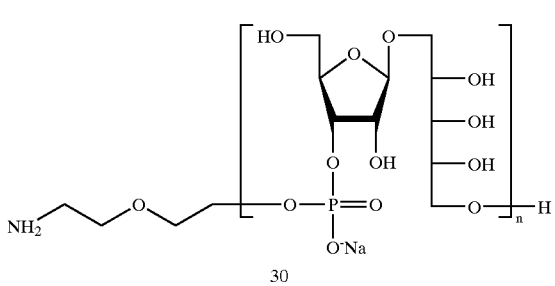

30

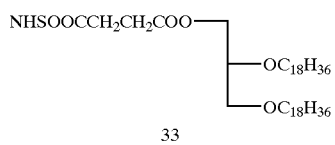

33

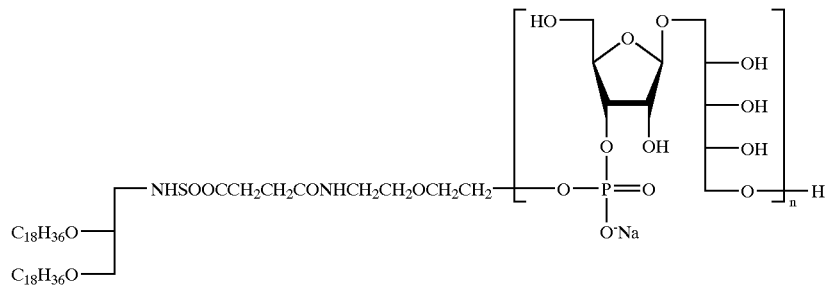

34

The conjugate of the synthetic oligosaccharide mixture and proteins can be diluted or reconstituted in an adequate physiological buffer and can be mixed with additives as adjuvants, preservatives, and others with the aim to obtain the final vaccine formulation.

Likewise, the vaccine can be mixed before or during the formulation process with other vaccines, from the type preparations become equal after the second doses. In both cases a high antibody titter was observed.

In the example of Sprague-Dawley rats, the vaccine prepared from the two conjugates differing in the carbohydrate-protein ratio, shown high anti-Hib antibody titters too.

In Balb c mice, the vaccine obtained from a similar conjugate induced high anti-capsular polysaccharide antibody titters.

The mixture of oligosaccharides 30 can be coupled to matrices as for example polyacrylamide. The product can be used for the detection of antibodies anti-Hib in immunized humans or in laboratory animals. The mixture can be coupled also to latex and be used in the detection of antibodies in sick or vaccinated people. The polyacrylamide activated according to N. Bovin (Glycoconjugate J., 1998, 15, 431–446) reacted with a mixture of oligosaccharides 30. The comparative ability of HbO-HSA, the recommended substance for the detection of anti-Hib antibodies, and the polyacrylamide conjugate of 30 is shown in FIG. 6. A better response-noise ratio was attained with the product containing the synthetic oligosaccharides.

WORKING EXAMPLES

Example 1

Synthesis of 5-O-allyl-2,3-di-O-benzyl-D-ribitol 11

Allylation.

100 g of methyl 2,3-O-isopropyliden-D-ribofuranoside were dissolved in 70 mL of allyl bromide and stirred in the presence of 75 mL of aqueous sodium hydroxide 50% and 2.6 g of tetrabutyl ammonium iodide during 12 hours. After this time, the stirring was stopped and the phases were separated. The aqueous phase was extracted with dichloromethane (70 mL) and the pooled organic phase was dried and evaporated.

Hydrolysis.

The resulting syrup was dissolved in 1.5 L of methanol. To this solution were added 3.6 mL aqueous sulfuric acid (0.4 N) and the mixture was refluxed for 3 hours. After the reaction finished, it was neutralized with sodium bicarbonate, the resulting salts were filtered and the solution was evaporated. The residue was extracted with ethyl acetate, dried and evaporated. The product was dried in vacuum for at least 2 hours.

Benzylation.

The product obtained was dissolved in 450 mL of dimethylformamide. The resulting solution was cooled to 0° C. and sodium hydride 50 g was added slowly. The mixture was stirred for 30 min and then benzyl chloride was dropped (150 mL). After 2 hours of stirring, 20 mL of methanol were dropped on the reaction. The resulting suspension was evaporated in vacuum, redissolved in dichloromethane and washed with water. The organic phase was dried with sodium sulfate and evaporated.

Hydrolisis.

The resulting syrup from the previous reaction was dissolved in 1.5 L of dioxane. HCl (2N, 1.5 L) was added and the system was heated at 75–80° C. After 2 hours, the reaction was stopped and the phases were separated. The aqueous phase was extracted twice with 200 mL of dichloromethane and the pooled organic phase was evaporated. The concentrated product was dissolved in dichloromethane (1 L) and washed successively with water (400 mL), saturated solution of sodium bicarbonate(300 mL) and water (400 mL), and finally is dried with sodium sulfate and evaporated.

Reduction.

The resulting syrup was dissolved in ethanol (800 mL) and the system was cooled to 20° C. Then 24 g $NaBH_4$ were added. The mixture was stirred for 1.5 hours at room temperature and after the reaction is finished the excess of borohydride was destroyed with acetic acid until to reach pH 7–8. The solution was filtered and evaporated. The residue was dissolved in 500 mL of dichloromethane, the organic solution was washed with water, dried with sodium sulfate and used in the following example.

Example 2

Purification of 5-O-allyl-2,3-di-O-benzyl-D-ribitol 11

To the dichloromethane solution of crude 5-O-allyl-2,3-di-O-benzyl-D-ribitol 11 from the previous example were added 300 g of silicagel and the mixture was stirred manually until the product was adsorbed in the solid phase. The suspension was evaporated in vacuum for the elimination of dichloromethane. The silicagel containing the product was placed in a percolator. The impurities were removed by extraction with cyclohexane for 48 hours. The solvent of extraction was change to dichloromethane for the extraction of the product giving a chromatographically pure pale yellow syrup. Yield 75–95%. NMR$^{13}$C δ 60.7(C-1), 70.2 (C-4), 71.0, 71.7, 72.0, 73.6 ($PhCH_2$C-5, $OCH_2$CH=), 79.2, 79.3 (C-2,3), 117.1 ($CH_2$=), 127.5–128.2 (Ph), 134.3 (CH=), 138.0, 138.1 (Cipso).

Example 3

Synthesis of 5-O-allyl-2,3,4-tri-O-benzyl-D-ribitol 14

Trytilation.

100 g of 5-O-allyl-2,3-di-O-benzyl-D-ribitol 11 from the previous example were dried in vacuum and dissolved in 600 mL of pyridine. To this solution were added 75 g of chlorotriphenylmethane and 0.5 g dimethylaminopyridine and the mixture was stirred at 50° C. for 6 hours. Once the reaction is finished, the solvent was evaporated and the residue was dissolved in 500 mL of dichloromethane, the solution was washed with water (1 L), dried and evaporated. The residue was dried in vacuum for 3 hours.

Benzylation.

The syrup from the previous reaction was dissolved in 300 mL of dimethylformamide and the solution was cooled to 5° C. Sodium hydride (25 g) was added slowly and the stirring was then continued for 30 minutes. Benzyl chloride (40 mL) was then added slowly and the stirring was maintained for 1 hour. After the reaction have finished, it was cooled again and 10 mL of methanol were slowly added in order to destroy the excess of reagents. The solvents were evaporated, and the residue was dissolved in 500 mL of dichloromethane, washed with 1 L of water. The organic phase was dried with sodium sulfate and evaporated.

Hydrolysis.

The residue was dissolved in acetic acid (1 L) and 110 mL of water, and the reaction was stirred at 80° C. for 1.5 hours. The solvent was eliminated by evaporation and the residue was dissolved in 500 mL of cyclohexane. The organic phase was cooled to 0–5° C. for 4 hours. and then filtered, washed with water, dried with sodium sulfate and evaporated. The product was obtained pure by distillation at 200–220° C. and 0.1 mm. Yield 80–90 g base on 100 g of ribose. NMR $^{13}$C δ 61.2 (C-1), 69.6, 71.8, 72.1, 72.3. 73.9 ($PhCH_2$C-5, $OCH_2$CH=), 78.0, 78.8, 78.9 (C-2,3,4), 116.8 ($CH_2$=), 127.5–128.2 (Ph), 134.7 (CH=), 138.0, 138.1, 138.2 (Cipso).

Example 4

Synthesis of 5-O-Allyl-2,3,4-tri-benzyl-1-O-(β-D-ribofuranosyl)-D-ribitol 4

Glycosylation.

The product of the previous example (370 g) was dissolved in 2.7 L of dried dichloroethane and transferred to a rector. The solution was cooled to 0–25° C., powder molecular sieves 4 Å (207 g) were added and after minutes, boron trifluoride etherate (407 mL) was added slowly at 15 mL/min. Finally D-ribofuranose peracetate 15 (370 g) dissolved in dried dichloroethane (1 L) was added slowly during 20 min. The reaction was stirred for 3 hours and surveyed by TLC hexanes/ethyl acetate (2/1). The plates were developed by charring with 5% $H2SO4_{(c)}$ in ethanol. Once the reaction was finished it was neutralized with triethylamine (222 mL) until pH 7 and then a saturated solution of sodium bicarbonate (800 mL) was added and the stirring was continued for 30 minutes. The pH of the reaction must be kept at neutrality. The content of the reactor was filtered in vacuum. The solid was washed twice with dichloroethane (200 mL) to extract any remaining product in the solid. The solid phase was discarded and the organic phase was extracted twice with water 600 mL, dried with sodium sulfate and evaporated in vacuum.

Deacetylation.

To the resulting syrup from the previous reaction dissolved in methanol (2 L), was added a solution of sodium methoxide (1%) in methanol until the pH attained 9. The reaction was continued up to almost 2 hours. Once finished, the reaction was neutralized with acid resin until the pH attained 6–7. The resin was eliminated by filtration in vacuum. The syrup (427 g) contain the desired product together with 5-O-Allyl-2,3,4-tri-O-benzyl-D-ribitol, D-Ribosa and other non determined impurities.

Example 5

Purification of 5-O-Allyl-2,3,4-tri-O-benzyl-1-O-($\beta$-D-ribofuranosyl)-D-ribitol 4

The syrup of the previous example was dissolved in dichloromethane (1 L). To the solution was added silicagel (1 kg) and the mixture was stirred manually until the product was adsorbed in the solid phase. The suspension was evaporated in vacuum for the elimination of dichloromethane. The resulting solid was dried in vacuum for 2 hours for removing any traces of dichloromethane.

The silicagel containing the product was placed in a percolator. The impurities were removed by extraction with cyclohexane for 48 hr. The solvent of extraction was change to chloroform for the extraction of the product giving a pale yellow syrup. Yield 238 g. NMR $^1$H $\delta$ 5.85 (m, 1H, CH=), 5.20 (m, 2H, CH$_2$=), 4.85 (s,1H,H-1'),$^{13}$C $\delta$ 62.8 (C-5'), 77.7, 77.9, 78.2 (C-2,3,4), 84.0 (C-4'), 107.2 (C-1').

Example 6

Synthesis of 5-O-allyl-2,3,4-Tri-O-benzyl-1-O-($\beta$-D-2',5'-di-O-benzyl-ribofuranosyl)-D-ribitol 5

Benzylation.

The compounds (200 g) resulting from the previous example was dissolved in toluene (2 L). To this solution was added Bu$_2$SnO (80 g) and the mixture was refluxed for 4 hours. NaH 50% (56 g) was added in small portion at room temperature, and the mixture was stirred at 80° C. for 30 minutes. Tetrabutyl ammonium iodide (62 g) was added and the mixture was stirred again for 1 hour. Benzyl chloride was then added (148 mL) and the reaction was continue with stirring at 80° C. for several hours. Similar additions of benzyl chloride were repeated at 30 min interval until TLC (hexanes/ethyl acetate-2/1) shown a major product consisting in a dibenzylated disaccharide. The reaction was cooled and neutralized with a methanolic solution of 1% HCl. Then the reaction was filtered through celite, and evaporated under reduced pressure. The resulting product that contains some salts was dissolved in ethyl acetate, filtered at reduced pressure and concentrated. The crude syrup was purified by column chromatography in a solvent system toluene-acetone 60/1. Pure 5 was obtained as a syrup (100 g). NMR-$^1$H $\delta$ 5.96 (m, 1H, —CH=), 5.18 (m, 2H, CH$_2$=), 5.02 (s, 1H, H-1)

Example 7

Synthesis of 2,3,4-Tri-O-benzyl-1-O-($\beta$-D-2',5'-di-O-benzyl-3'-O-triethylammonium phosphonate-ribofuranosyl)-D-ribitol (19)

Isomerization of allyl group.

20 g of the resulting syrup from the previous example was dried in high vacuum for 2 hours. The syrup was dissolved in dried Dimethylsulfoxide (100 mL) and potassium t-butoxide (6.4 g) was added. The reaction was stirred at 100° C. for 1 hour and then added to 250 mL of ice-water. Concentrated hydrochloric acid was added drop by drop to reach a pH 7. The mixture was extracted 3 times with 80 mL of diethylether. The organic phase were pooled, dried with sodium sulfate and evaporated.

Phosphonylation.

A solution of imidazol (1.5 g) in dried acetonitrile (34 mL), was cooled to 0° C. Phosphorous trichloride (0.56 mL) and triethylamine (3.1 mL) were added. The resulting solution was stirred for 15 minutes. The disaccharide from the previous reaction was added to this mixture dissolved in dried acetonitrile (3 mL). The resulting mixture was stirred for 15 minutes at room temperature and was stopped by the addition of a 1M solution of triethylammonium bromide. Stirring was continued for 10 minutes, the dichloromethane was added and the phases were separated. The organic phase was washed with cool solution of triethylammoniun bicarbonate, dried and evaporated.

Hydrolysis of propenyl group.

The product was dissolved in acetic acid 60% and was stirred at 70° C. for 30 minutes. The solvent was removed by evaporation and the product was dissolved in dichloromethane, washed with triethylammoniun bicarbonate, dried and evaporated. Column chromatography of the resulting product gave the pure compound with a yield between 70–85%. NMR $^1$H $\delta$ 6.85 (d, H-P), 4.95 (s, H-1), 4.60 (m, H-3), 2.93 (q, NCH$_2$CH$_3$) 1.20 (t, NCH$_2$CH$_3$). $^{13}$C $\delta$ 105.9 (C-1).

Example 8

Polycondensation Reaction Between 19 and 26 (Ratio 10-1)

To a solution of compound 19 (1 g) in pyridine-triethylamine (10-1, 1 mL) was added trimethylacetyl chloride (0.14 mL) and the reaction was stirred for 20 minutes. The spacer 26 (29.2 mg) was added and a new quantity trimethylacetyl chloride (0.9 mL) and the reaction was stirred for 1 hour. A solution of I$_2$ (1.1 g) in pyridine-water was added (7.3 mL; 20-1) and the reaction was stirred for 30 minutes. The mixture was diluted with dichloromethane, washed with solutions of sodium thiosulfate (1M) and with a cold solution of triethylammonium bromide (0.5M), then is dried with sodium sulfate and evaporated. The resulting product was dissolved in methanol and chromatographed in a column of Sephadex LH-20 in the same solvent. The fractions containing the oligomers were pooled and evaporated. Yield 80%.

Example 9

Polycondensation Reaction Between 19 and 26 (Ratio 10-1)

To a solution of compound 19 (1 g) and the spacer 26 (14.6 mg) in pyridine-triethylamine (10-1, 1 mL) was added trimethylacetyl chloride (0.23 mL) and the reaction was stirred for 2 hours. A solution of I$_2$ (1.1 g) in pyridine-water was added (7.3 mL; 20-1) and the product was treated in a similar way as in the example 8.

Example 10

Polycondensation Reaction Between 19 and 26 (Ratio 5-1)

To a solution of compound 19 (1 g) and the spacer 24 (29.2 mg) in pyridine-triethylamine (10-1, 1 mL) was added trimethylacetyl chloride (0.23 mL) and the reaction was stirred for 2 hours. A solution of I$_2$ (1.1 g) in pyridine-water was added (7.3 mL; 20-1) and the product was treated in a similar fashion as in the example 8.

Example 11

Polycondensation Reaction Between 23 and 26 (Ratio 5-1, Solvent Pyridine)

To a solution of compound 23 (1 g) and the spacer 26 (29.2 mg) in pyridine (1 mL) was added trimethylacetyl chloride (0.23 mL) and the reaction was stirred for 2 hours. A solution of $I_2$ (1.1 g) in pyridine-water was added (7.3 mL; 20-1) and the product was treated in a similar way as in the example 8.

Example 12
Polycondensation Reaction Between 19 and 24 (Ratio 5-1, Solvent Pyridine)

To a solution of compound 19 (1 g) and the spacer 24 (29.2 mg) in pyridine (1 mL) was added trimethylacetyl chloride (0.23 mL) and the reaction was stirred for 2 hours. A solution of $I_2$ (1.1 g) in pyridine-water was added (7.3 mL; 20-1) and the product was treated in a similar fashion as in the example 8.

Example 13
Hydrogenation Reaction of the Products from the Examples 8–12

The crude product of the previous examples 8–12 was hydrogenated in a mixture ethyl acetate-ethanol-water-acetic acid (1-2-2-0.1) with Palladium on carbon 10%. Finally the product was purified by ion-exchange chromatography on sephadex C-25 Na. Lyophilized product was characterized by NMR and shown the basic repeating unit Rib-Rib-phosphate and the spacer. Active fractions were obtained after a diafiltration and ultrafiltration process, first through a cutoff membrane of 1000 and the retentate by a 10000 cutoff membrane. The solution that pass through the 10000 membrane were pooled and lyophilized giving the final 28 with and overall yield that depending on reaction conditions are between 20–80% base on the departing disaccharide. NMR $^1H$ δ 5.12 (H-1), 4.60 (H-3), 3.29 ($CH_2NH_2$). $^{31}P$ δ 2.14 (spac-P-Rib) 0.74 (Ribitol-P-Rib).

Example 14
Synthesis of a Derivative 5-(3-maleimidopropionamido)-3-oxapentyl oligo ribosil ribitol phosphate 30

To a solution of the previous example (3.34 mg, 1.73 μmol) in bidistilled water (0.1 mL), was added 0.7 mg (2.62 μmol) of N-hydroxysuccinimidyl β-maleimidopropionate 27 dissolved in N,N-dimethylformamide (0.4 mL). After 4 hours of reaction, the solution was evaporated in vacuum, resuspended in distilled water (0.5 mL), and centrifuged (10 minutes, 3500 rpm). The supernatant was diluted with water and ultrafiltered in an Amicon equipment with cutoff membrane of 1000. The retentate was lyophilized. Yields are between 85 y 95%. NMR: $^1H$, δ 6.95 (s, 2H, CH=CH), 5.01 (s, H-1) 3.41 (t, 2H, $CH_2NH$), 2.56 (t, 2H, $CH_2a$).

Example 15
Analysis of the Products Obtained from Example 13 by ion Exchange Chromatography The products of example 8–12 hydrogenated and as a sodium salts were analyzed by ion exchange chromatography in a HR5/5 mono Q column with a lineal gradient of sodium chloride (P. Constantino, y col., Vaccine 1999, 17, 1251–1263). The elution chromatographic profile of example 8 is represented in FIG. 1B and shown fragments of different sizes. If they are compared with the results reported in the literature and FIG. 1A representing a chromatogram of a pentamere, it can be concluded that in the mixture are represented fragments from 4–5 repeating units to more than 20.

Example 16
Conjugation to Neiseria meningitidis Outer Membrane Protein

Neisseria meningitidis Outer Membrane Protein Complex (OMPC) 400 mg was dissolved in 80 mL of PBS buffer pH 8 previously flushed with $N_2$ (g). The solution was flushed with $N_2$ (g) for 5 minutes while stirring in an ice-water bath. A 1.6 mL solution of DSP in dimethylformamide was added and the mixture was gentle stirred at 4° C. for 2 hours. A 1.6 mL solution of DTT in PBS was added and the stirring at 4° C. was continued for 1 hour. The resulting suspension was transferred to a centrifuge flask containing 20–400 mL of cold ethanol. The flask was centrifuged at 1800 rpm and 4° C. for 30 minutes and the supernatant was discarded. A new portion of ethanol was added to the solid and the centrifugation process was repeated again after to add 200–400 mL of ethanol. The precipitate was resuspended in 80 mL of PBS buffer pH=7–9. To the resulting solution was added the synthetic oligosaccharide 30 and the stirring was continued for 1–48 hours. Once the process was finished, the ethanolic precipitation-centrifugation operations were repeated following by a diafiltration using a 30 000 cutoff membrane. The retentate was reconstituted in a PBS buffer to a concentration of Hib 40–80 μg per mL

Example 17
Conjugation to Tetanus Toxoid

A solution of tetanus toxoid at a concentration 5 mg/mL in PBS pH 8 was buubled with $N_{2(g)}$ for 5 minutes. While maintaining a stirring in a ice-water bath, a 1.6 mL solution of DSP in dimethylformamide was added and the mixture was gentle stirred at 4° C. for 2 hours. A 1.6 mL solution of DTT in PBS was added and the stirring at 4° C. was continued for 1 hour. The resulting solution was transferred to an ultrafiltration equipment with a 10000 cutoff membrane. The solution was diafiltrated several times by adding fresh buffer previously bubble with $N_{2(g)}$ until the solution that past through the membrane was negative to Elman test. To the resulting solution was added the synthetic oligosaccharide 30 and the stirring was continue for 1–48 hours. Once the process was finished the solution was diafiltrate again until the solution that past the membrane was negative to phenol-sulfuric test for sugars. Finally the solution was reconstituted in PBS buffer to a concentration of Hib 40–80 μg per mL.

Example 18
Conjugation to Dioctadecil Glicerol Hemisuccinate

The product of the example 8 (10 mg) was dissolved in 1 mL of dimethylformamide and added to a solution of dioctadecil glicerol hemisuccinate as N-hidroxisuccinimide ester 31. To the solution was added ethyl diaminopropylcarbodiimide (5 mg) and the reaction was stirred for 6 hours. A new portion of carbodiimide was added and the stirring was continued for 6 hours. The solvent was evaporated and the mixture was applied to a column of C18-silicagel (1 g). The elution with water removed the oligosaccharide. The product was eluted with a gradient concentration of metanol-water. Yield 85%. NMR $^1H$ δ 5.12 (H-1), 4.60 (H-3), 3.40 ($CH_2NH$), 1.30 ($CH_2$), 0.90 ($CH_3$).

Example 19
Preparation of a Vaccine without Adjuvant

The immunogen of the example 16 dissolved in a phosphate buffer at a concentration 40 μg per mL was diluted under aseptic conditions at 4–8° C. with a solution of bidistilled water. The suspension was stirred for 10 minutes. The final concentration of Hib antigen was determined by estimation of Ribose and total proteins and could be readjusted by adding more buffer solution until a final Hib antigen concentration of 20 mg per mL. Tiomersal was added to a final concentration of 0.1–0.001%. The resulting suspension is the final bulk of an anti-Hib conjugate vaccine without adjuvant

Example 20
Preparation of anti-Hib Vaccine in Alumina as Adjuvant

The immunogen of the example 16 dissolved in a phosphate buffer at a concentration 40 µg per mL, was mixed under aseptic conditions at 4–6° C. with an equal volume of alumina 1–0.01 mg per mL in distilled water. The stirring was maintained for 20 min at 4–8° C. The final concentration of Hib was determined by estimation of Ribose and total proteins and could be readjusted by adding more buffer solution until a final antigen Hib concentration of 20 mg per mL. Tiomersal was added to a final concentration of 0.1–0.001%. The resulting suspension is the final bulk of an anti-Hib conjugate vaccine in alumina.

Example 21
Preparation of a Combined anti-Hib and antimeningococcus B Vaccine The immunogen of the example 16 dissolved in a phosphate buffer at a concentration 80 µg per mL, was mixed under aseptic conditions at 4–6° C. with a bulk solution of Outer Membrane Protein Complex (OMPC) of *Neisseria meningitidis* type B currently employed in VAMEMGOC BC at a concentration in PBS of 100–200 mg per mL. After 20 minutes of homogenization by soft magnetic stirring, the content of the reaction was mixed with equal volume of alumina 1–0.01 mg per mL in distilled water. The stirring was maintained for 20 min at 4–6° C. The final concentration of the antigen Hib was determined by estimation of Ribose and total proteins by Lowry, and could be readjusted by adding more buffer solution until a final antigen Hib concentration of 20 mg per mL. Tiomersal was added to a final concentration of 0.1–0.001%. The resulting suspension is the final bulk of a combined anti-Hib and anti-meningococcus B in alumina.

Example 22
Preparation of a Combined Vaccine anti-Hib and anti-DTP

The immunogen of the example 16 dissolved in a phosphate buffer at a concentration 80 µg per mL, was mixed under aseptic conditions at 4–6° C. with a bulk solution of DTP at a 4× concentration. After 20 minutes of homogenization by soft magnetic stirring, the content was mixed with equal volume of alumina 1–0.01 mg per mL in bidistilled water. The stirring was maintained for 20 minutes at 4–6° C. The final concentration of Hib was determined by estimation of Ribose and total proteins by Lowry and could be readjusted by adding more buffer solution until a final antigen Hib concentration of 20 mg per mL. Tiomersal was added to a final concentration of 0.1–0.001%. The resulting suspension is the final bulk of a combined anti-Hib and anti-DTP in alumina.

Example 23
Immunological Essays of Vaccines Prepared from Synthetic oligosaccharide Mixture and OMP The vaccine of examples 19 and 20 were immunized at a dose 1 µg o 2 µg of antigens. The animals used in these experiments were rabbits, rats and mice. 2 immunizations were performed at 4 weeks interval with bleeding at 0, 28 and 42 days. The blood was collected and centrifuged at 3500 r.p.m. for 20 minutes. The sera were diluted 10 times and stored at −40° C.

The antibody response was measured by an indirect ELISA using Hib-HSA as coating antigen. The results are shown in FIGS. 2–5.

Example 24
Conjugate Between the Mixture of Synthetic oligosaccharides and p-nitrophenylacrylate The mixture of oligosaccharides from example 13 (10 mg) was dissolved in dimethylformamide and was added to a solution of nitrophenylacrylate (10–30 mg) in dimethylformamide (1 mL). 0.1–0.5 mL of triethylamine was added and the reaction was maintained with stirring for 16 hours. Ammonia 0.1–0.5 mL was added and the stirring was continued for 24 hours. The solution was applied on a column of sephadex LH-20 in acetonitrile. The elution was performed with acetonitrile-water. Fractions positive in the orcinol assay for ribose were pooled and lyophilized. The yield is usually higher than 80%.

Example 25
Ability of the Synthetic Oligosaccharide Conjugate to Detect anti-Hib Antibodies A solution of the product from the previous example in a carbonate-bicarbonate buffer was applied in a concentration 1–100 µg per mL on one half of a 96 well plate. On the other half of the plate was applied the antigen HbO-HSA at recommended concentration. An assay ELISA is carried out using the sera of mice immunized with a vaccine containing the natural capsular polysaccharide coupled to tetanus toxoid. The results obtained are shown in FIG. 6.

Figure 1B:
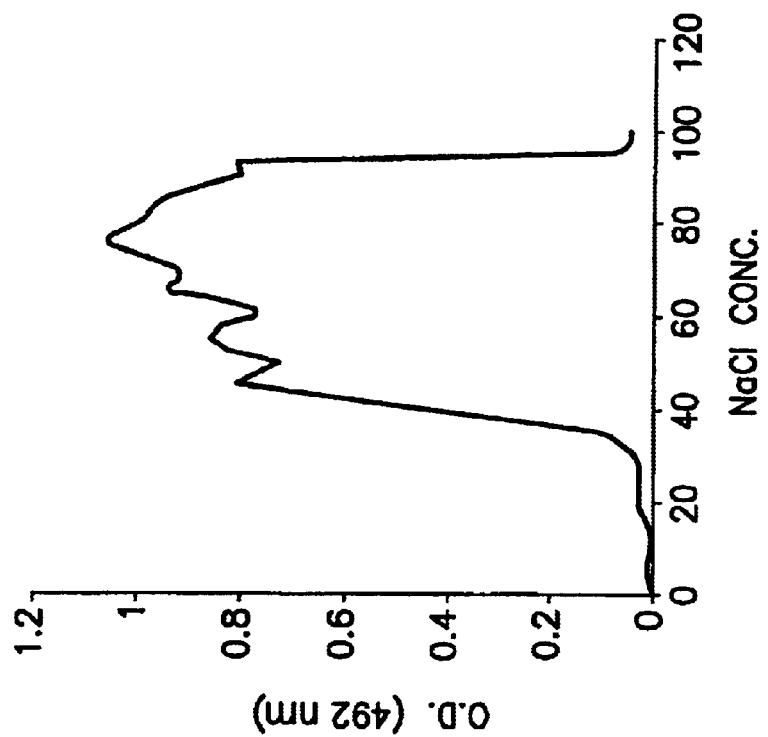
FIG. 1B. Typical chromatogram of the oligomeric fractions obtained in Example 15 by ion exchange chromatography on Mono Q HR 5/5 with a lineal gradient of NaCl 0–500 mM.
Figure 1A:
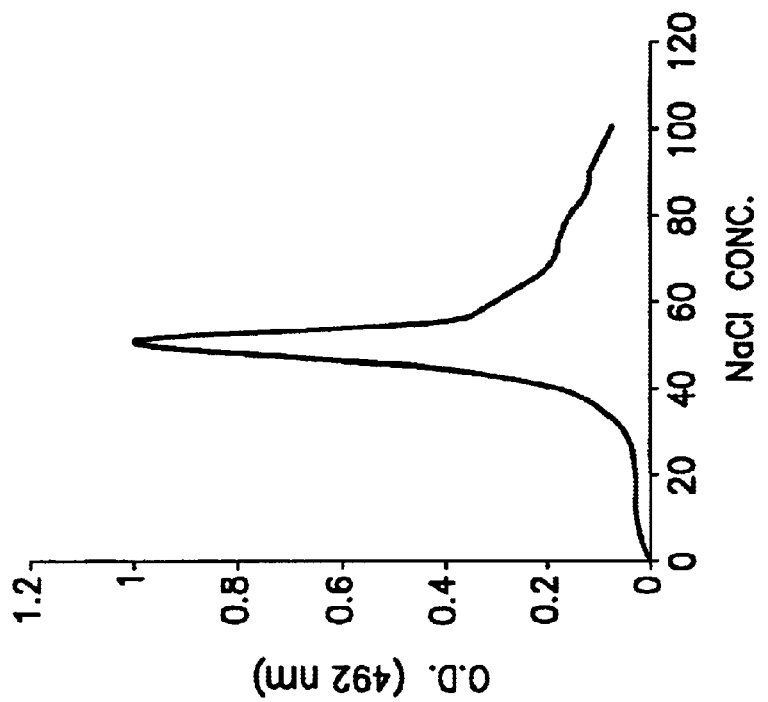
FIG. 1A. Typical chromatogram of a pentamere.
Figure 2:
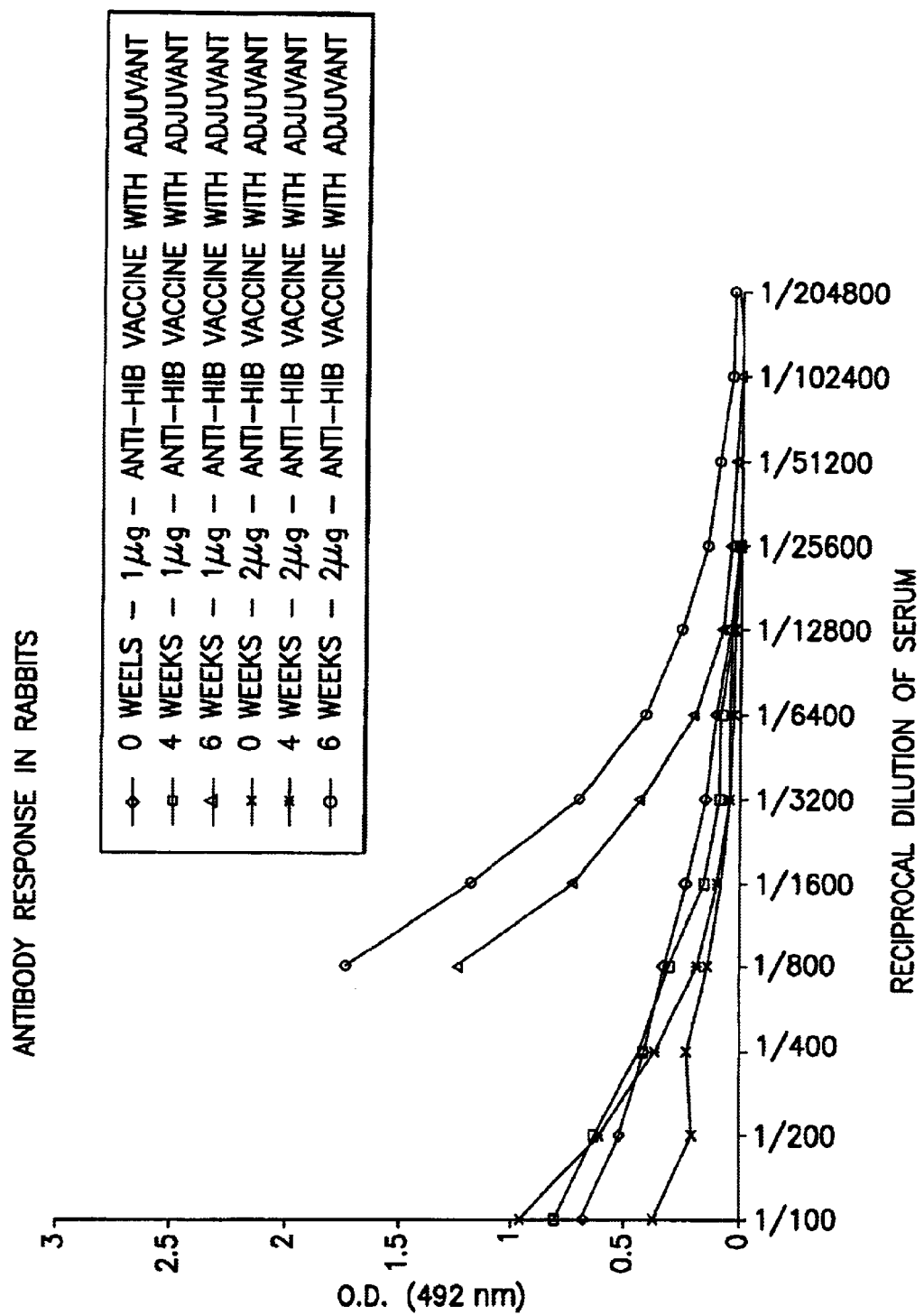
FIG. 2. Antibody response in rabbits immunized with the vaccine of the Example 20.
Figure 3:
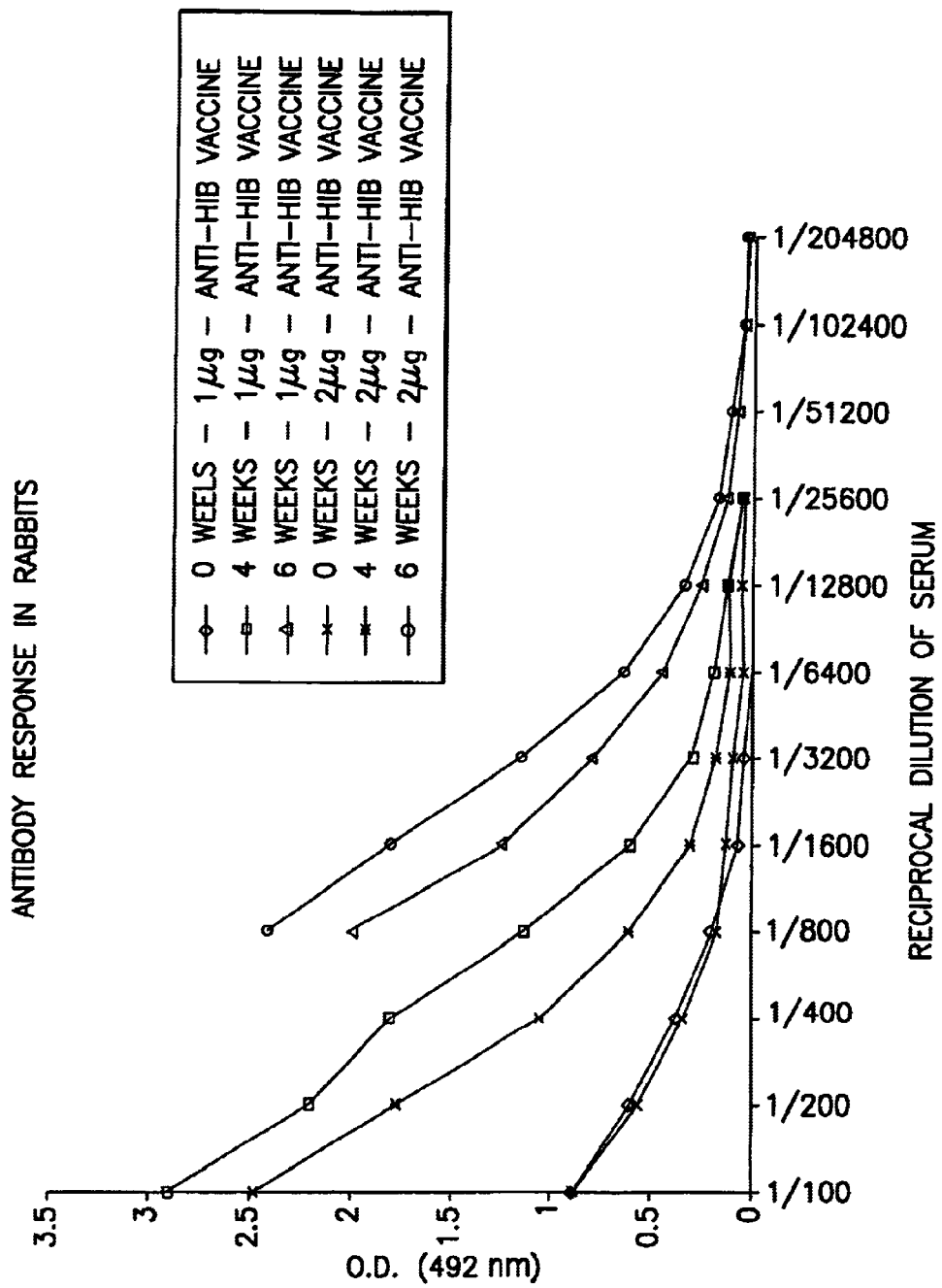
FIG. 3. Antibody response in rabbits immunized with the vaccine of Example 19.
Figure 4:
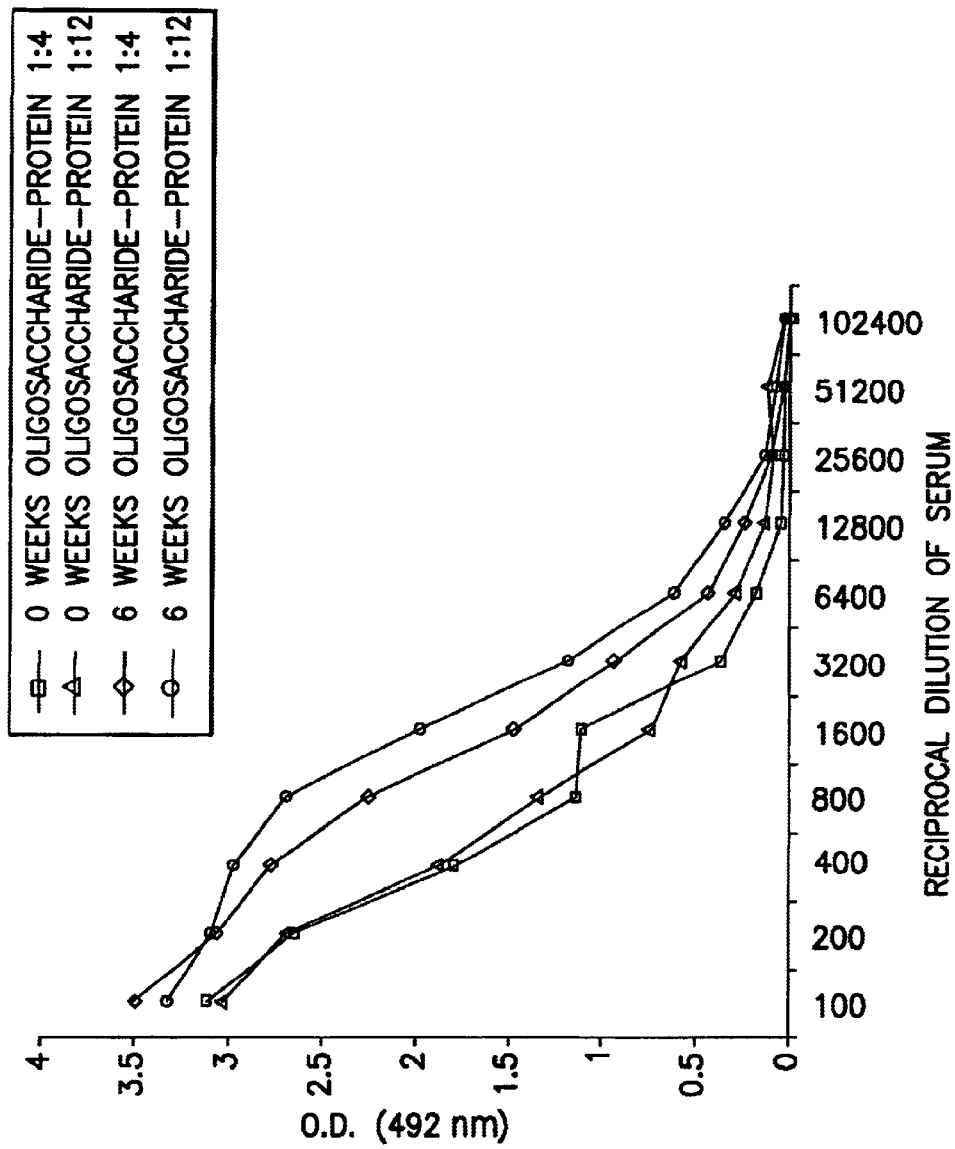
FIG. 4. Comparison of oligosaccharide-protein mixture at different concentrations and times.
Figure 5:
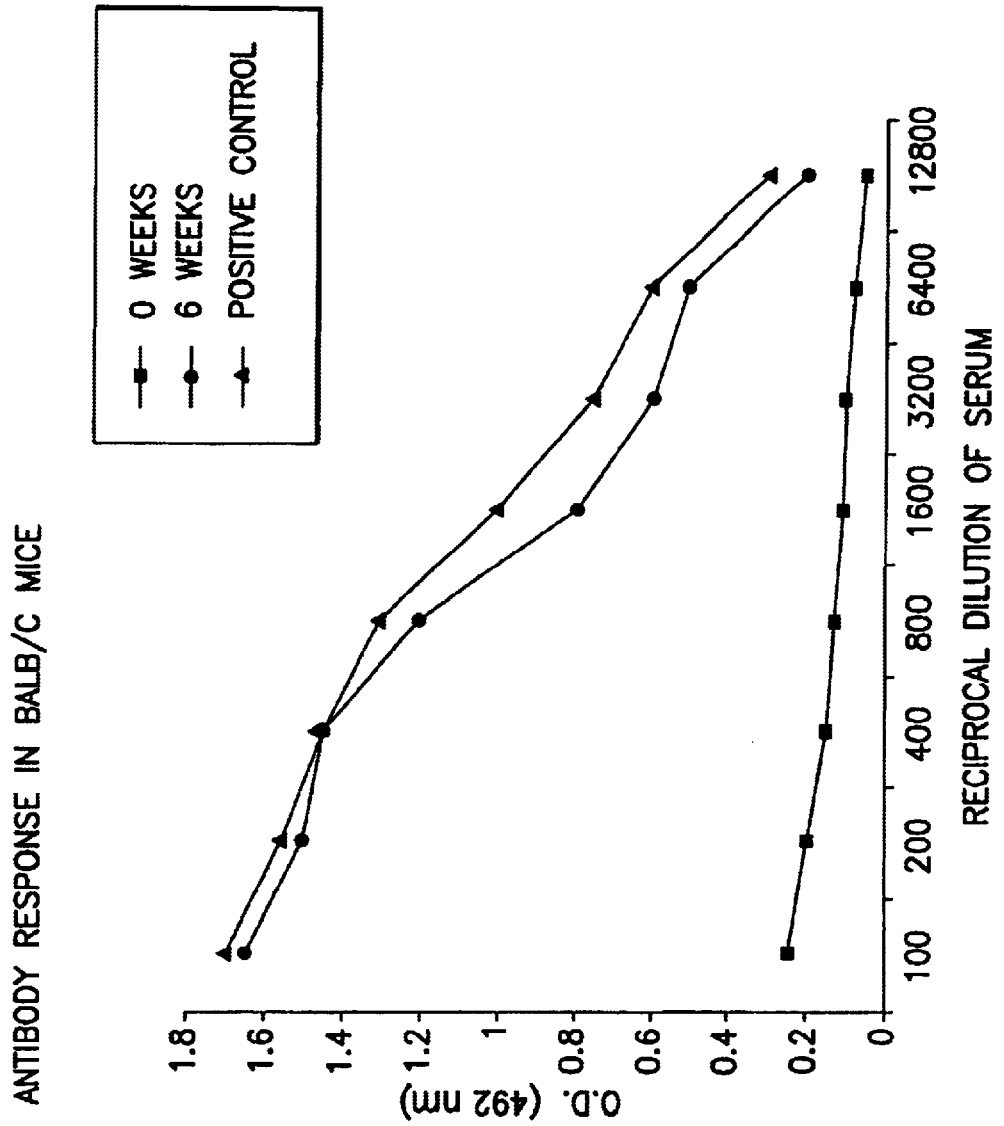
FIG. 5. Antibody response in Balb C mice immunized with the vaccine of example 19.
Figure 6:
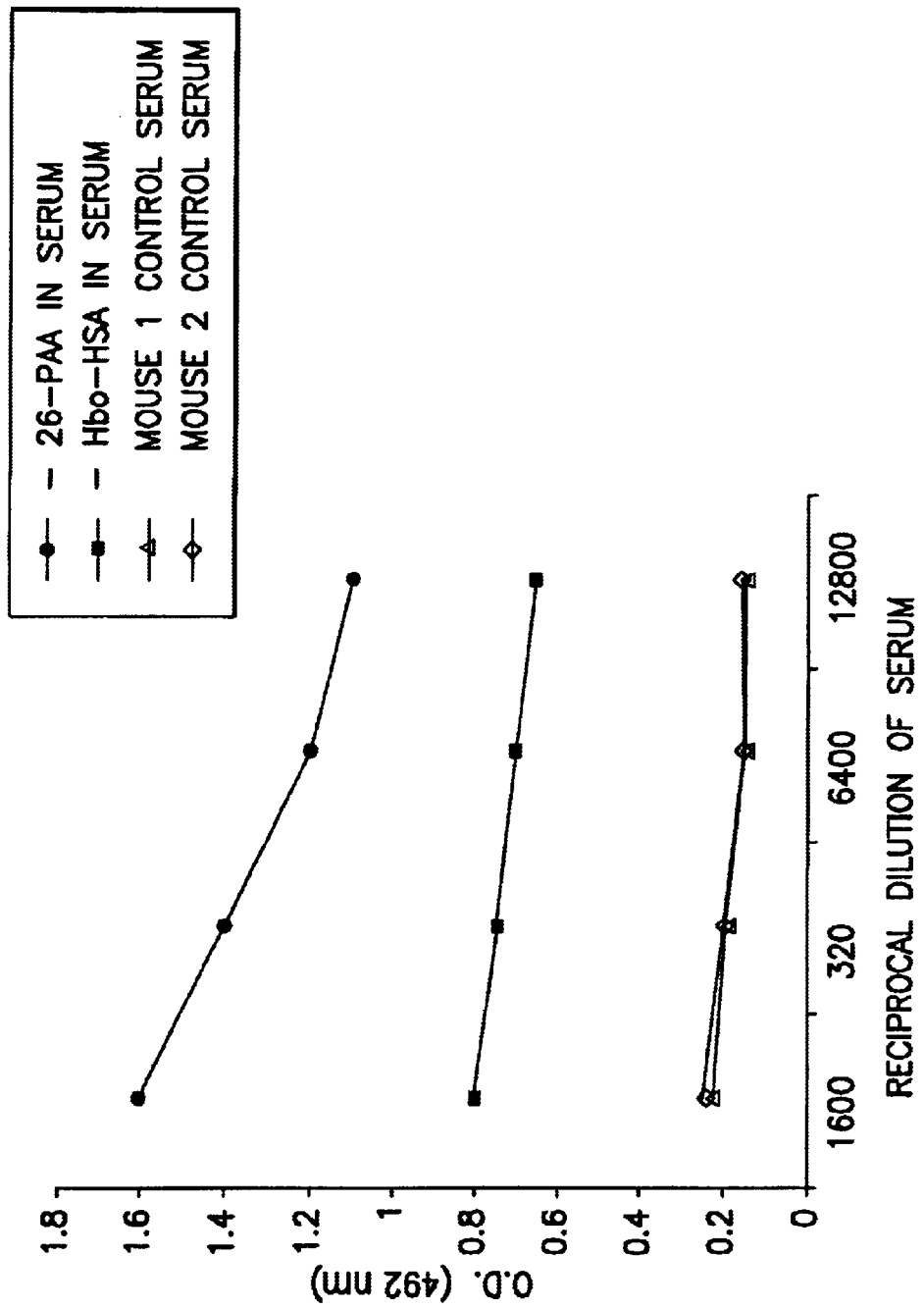
FIG. 6. Ability of the conjugate 26-PAA for detecting antibodies anti-Hib.

What is claimed is:

1. A procedure for synthesizing a mixture of oligomeric chains comprising repeating units of formulas (phosphate-ribose-ribitol) or (ribose-ribitol-phosphate) comprising the step of:

beginning a polycondensation reaction in a mixture comprising disaccharide derivatives of the structure 19 or 23:

$$[19]$$

(structure showing a ribose ring with BnO, O, OBn substituents, linked via O to a ribitol chain bearing OBn, OBn, OBn, OH groups, with H—P(=O)—O⁻Et₃NH⁺ phosphite group)

-continued

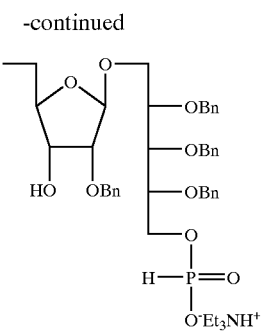

[23]

in the presence of a reaction promoter, a basic solvent, and a spacer that participates in the reaction as an acceptor for quenching the growth of the oligomeric chains.

2. The procedure according to claim 1 wherein the disaccharide intermediate of the structure 19 or 23 and the promotor are in a molar ratio of 1/1 to 1/3.

3. The procedure according to claim 1 wherein the promoter is a sterically hindered acid chloride.

4. The procedure according to claim 1 wherein the promoter is pivaloyl chloride or adamantane-1-carbonyl chloride.

5. The procedure according to claim 1 wherein the disaccharide intermediate of the structure 19 or 23 and the spacer are in a molar ratio of 5/1 to 10/1.

6. The procedure according to claim 1 wherein the disaccharide derivative is of the structure 19, and the spacer is of the structure 24,

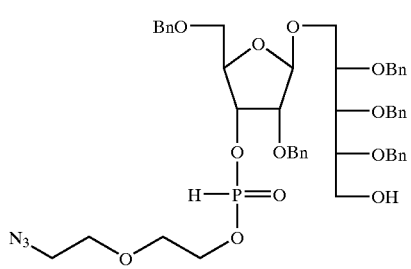

the promoter is pivaloyl chloride, and the solvent is pyridine.

7. The procedure of claim 1 further comprising the steps of: oxidizing the phosphonate groups of the obtained oligomeric derivatives from disaccharide derivative 19 or 23 to form phosphate groups, hydrogenation to remove the benzyl protective groups, deprotection or activation of the spacer, and elimination of oligomeric chains in the mixture that are less than 4 or more than 25 repeating units.

\* \* \* \* \*